(12) United States Patent
Gomez

(10) Patent No.: US 11,470,987 B1
(45) Date of Patent: Oct. 18, 2022

(54) CHAMELEON SOLE STATION FOOTWEAR APPARATUS

(71) Applicant: Abdul Luke Gomez, San Diego, CA (US)

(72) Inventor: Abdul Luke Gomez, San Diego, CA (US)

(73) Assignee: Abdul Luke Gomez, San Diego, CA (US)

( * ) Notice: Subject to any disclaimer, the term of this patent is extended or adjusted under 35 U.S.C. 154(b) by 0 days.

(21) Appl. No.: 17/529,024

(22) Filed: Nov. 17, 2021

(51) Int. Cl.
| | | |
|---|---|---|
| *A47F 3/02* | (2006.01) | |
| *G05B 15/02* | (2006.01) | |
| *A43B 3/24* | (2006.01) | |
| *A43B 13/36* | (2006.01) | |
| *G07F 9/00* | (2006.01) | |
| *A43D 1/02* | (2006.01) | |
| *G06Q 20/18* | (2012.01) | |

(52) U.S. Cl.
CPC ............... *A47F 3/02* (2013.01); *A43B 3/244* (2013.01); *A43B 13/36* (2013.01); *A43D 1/025* (2013.01); *G05B 15/02* (2013.01); *G07F 9/009* (2020.05); *G05B 2219/45243* (2013.01); *G06Q 20/18* (2013.01)

(58) Field of Classification Search
CPC ......... G07F 11/70; G07F 9/009; A43B 13/36; A43B 3/244; A43D 1/025; G05B 2219/45243
USPC ........................................................ 700/233
See application file for complete search history.

(56) References Cited

U.S. PATENT DOCUMENTS

| | | | | |
|---|---|---|---|---|
| 2,407,189 | A * | 9/1946 | Taber, Jr. ................. | A43B 7/36 36/4 |
| 3,775,793 | A * | 12/1973 | Casavant ............. | A43D 11/003 12/1 R |
| 5,339,252 | A * | 8/1994 | White .................... | A43D 1/025 700/98 |
| 8,170,705 | B2 * | 5/2012 | Koelling ................. | G07F 17/04 702/33 |
| 11,134,863 | B2 * | 10/2021 | Penta .................... | A61B 5/1072 |
| 2006/0150399 | A1 * | 7/2006 | Koyama ................. | G07F 11/70 29/700 |
| 2013/0006413 | A1 * | 1/2013 | Canter .................... | G07F 9/002 700/231 |
| 2014/0259459 | A1 * | 9/2014 | Ianchulev ............ | A43D 25/188 12/18.1 |
| 2015/0101133 | A1 * | 4/2015 | Manz ................... | B29D 35/146 12/142 R |

* cited by examiner

*Primary Examiner* — Timothy R Waggoner
(74) *Attorney, Agent, or Firm* — Marshall, Gerstein & Borun LLP

(57) ABSTRACT

A footwear apparatus, comprising receptacles, having a mechanism that automatically removes and replaces interchangeable sole footwear parts; an automatic complete new sole dispenser; an automatic new sole heel dispenser; a complete old sole recycling automatic ejection component; an old sole heel dispenser automatic ejection component; a computer-implemented method for serving footwear and footwear soles to consumers from a vending machine; a computer-implemented foot scanning device, wherein said apparatus is comprised of a configuration to automatically replace the sole or partial sole of a pair or pairs of footwear.

28 Claims, 5 Drawing Sheets

CHAMELEON SOLE STATION FOOTWEAR APPARATUS

BACKGROUND OF THE INVENTION

1. Field of the Invention

Figure 1:
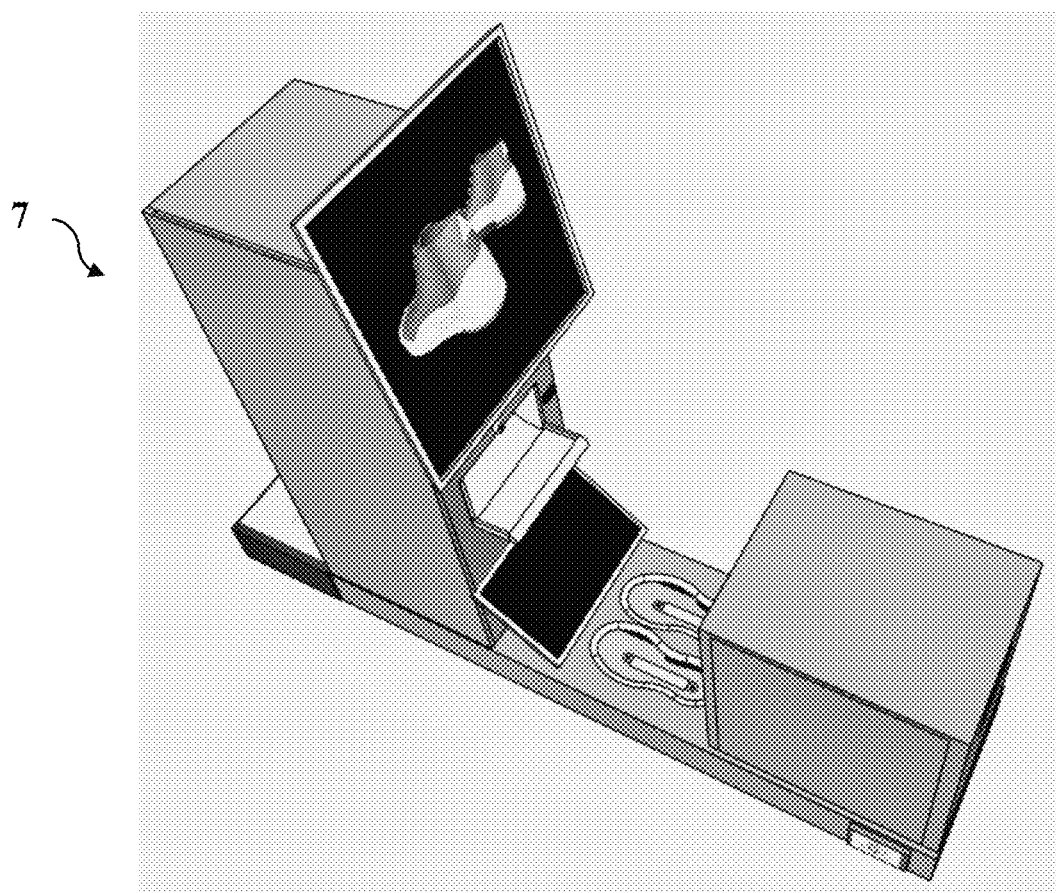

The present invention relates generally to footwear and more specifically it relates to a novel footwear sole apparatus that allows consumers to automatically interchange different soles or sole parts using the same pair of footwear thus automating interchangeable footwear sole replacement and increasing the versatility, longevity and comfort of a single pair or multiple pairs of footwear depending on the consumer's needs. Moreover, some versions of this novel footwear sole apparatus automatically measure and report on consumer shoe size, dispense new pairs of shoes, dispense standalone interchangeable shoe inserts, and temporarily store old shoes destined for retrofitting.

2. Description of the Related Art

Any discussion of the prior art throughout the specification should in no way be considered as an admission that such prior art is widely known or forms part of common general knowledge in the field.

Footwear has been in use for years. It was created to provide protection and comfort to the human foot. The sole is the bottommost part of the shoe or footwear. Typically, consumers purchase new footwear once their current footwear soles wear out, for safety, comfort and/or aesthetic reasons. Consumers also purchase different pairs of shoes based upon the specific type of sole that each pair distinctly offers such as spiked soled shoes for golf or track running, cleat soled shoes for soccer or football, traction-enhanced soles for trail running, corrective soled shoes to address foot related conditions, etc.

Current footwear soles are not suitable because they are not customizable. Per the examples in the previous paragraph, consumers must purchase multiple pairs of shoes to participate in diverse activities. Once the sole on a favorite pair of shoes wears out, it is typically thrown away even though the upper might still be in good condition and despite the fact that the shoe might otherwise be of great comfort and/or sentimental value to the consumer. There is currently no apparatus that allows consumers to automatically and repeatedly replace the soles of their interchangeable sole shoes. The apparatus referenced in this specification enables a shoe equipped with interchangeable soles to have its sole automatically replaced.

With the Chameleon Sole Station footwear apparatus, shoes with interchangeable sole functionality can now have their soles replaced in an automated manner instead of a consumer having to buy multiple pairs of footwear or manually interchange soles. With this apparatus, the consumer can change the entire sole or parts of the sole automatically to accommodate his/her needs or preferences. Some versions of the Chameleon Sole Station can allow the consumer to obtain foot size measurement, standalone interchangeable soles, and/or a complete new pair(s) of interchangeable sole footwear. For some versions of the Chameleon Sole Station, consumers will also be able to leave old pairs of shoes with noninterchangeable soles to be temporarily stored in the Chameleon Sole Station before being transported offsite to be retrofit into interchangeable sole shoes.

In these respects, the Chameleon Sole Station footwear apparatus according to the present invention substantially departs from the conventional concepts and designs of the prior art, and in so doing provides an apparatus primarily developed for the purpose of automating interchangeable footwear sole replacement and increasing the versatility, longevity, and comfort of a single pair or multiple pairs of footwear.

BRIEF SUMMARY OF THE INVENTION

In view of the foregoing disadvantages inherent in the known types of prior art, the present invention provides a new footwear sole apparatus wherein the same can be utilized for automating interchangeable footwear sole replacement and increasing the versatility, longevity and comfort of footwear. Moreover, some versions of this novel footwear sole apparatus automatically measure and report on consumer shoe size, dispense new pairs of shoes, dispense standalone interchangeable shoe inserts, and temporarily store old shoes destined for retrofitting.

The general purpose of the present invention, which will be described subsequently in greater detail, is to provide a new interchangeable footwear sole apparatus that has many novel features that result in a new footwear sole apparatus which is not anticipated, rendered obvious, suggested, or even implied by any of the prior art patents, either alone or in any combination thereof.

To attain this, the present invention generally comprises an automatic footwear sole replacement apparatus with receptacles, having a mechanism that removes and replaces sole parts as well as a storage compartment(s) for recycling old sole parts wherein said apparatus is comprised of a configuration to automatically replace the sole or partial sole of a pair or pairs of footwear.

Some versions of the Chameleon Sole Station will also comprise a display screen; a foot scanning device; one or more multi-functional camera scanners; new shoe vending; replacement sole vending; a payment reader; a built-in chair; foot fixation members if deemed necessary; a power cord; and a storage compartment for refurbish request shoes.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a footwear sole apparatus that will overcome the shortcomings of the prior art, automating interchangeable footwear sole replacement.

A second object is to provide a footwear sole apparatus that automatically obtains and processes consumer foot data, and generates output based on consumer foot attributes, Another object is to provide a footwear apparatus that dispenses new pairs of footwear.

A further object is to provide a footwear apparatus that dispenses standalone interchangeable footwear soles and partial soles.

An additional object is to provide a footwear apparatus that includes temporary storage where consumers can leave old pairs of footwear with noninterchangeable soles that will be transported offsite to be retrofit into interchangeable sole footwear.

A sixth object is to provide an improvement to the versatility of footwear.

A seventh object is to provide an improvement to the longevity of footwear.

An eighth object is to provide a footwear apparatus that improves the duration of consumer comfort with a preferred pair or pairs of shoes.

A further object is to maintain the aesthetic appearance of a pair or pairs of shoes over time.

An additional object of the present invention is to provide a footwear apparatus that meets the needs of consumers with orthopedic issues or disabilities.

An additional object of the present invention is to provide a recycling method for old interchangeable sole footwear parts.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE SEVERAL VIEWS OF THE DRAWING(S)

Various other objects, features and attendant advantages of the present invention will become fully appreciated as the same becomes better understood when considered in conjunction with the accompanying drawings, in which like reference characters designate the same or similar parts throughout the several views.

The bottom of the apparatus is flat and unadorned. FIGS. 2-5 include sectional detail of the complete new sole dispenser, new sole heel dispenser, and new footwear and standalone sole vending machine, as these interior structures form part of the claimed apparatus.

Figure 2:
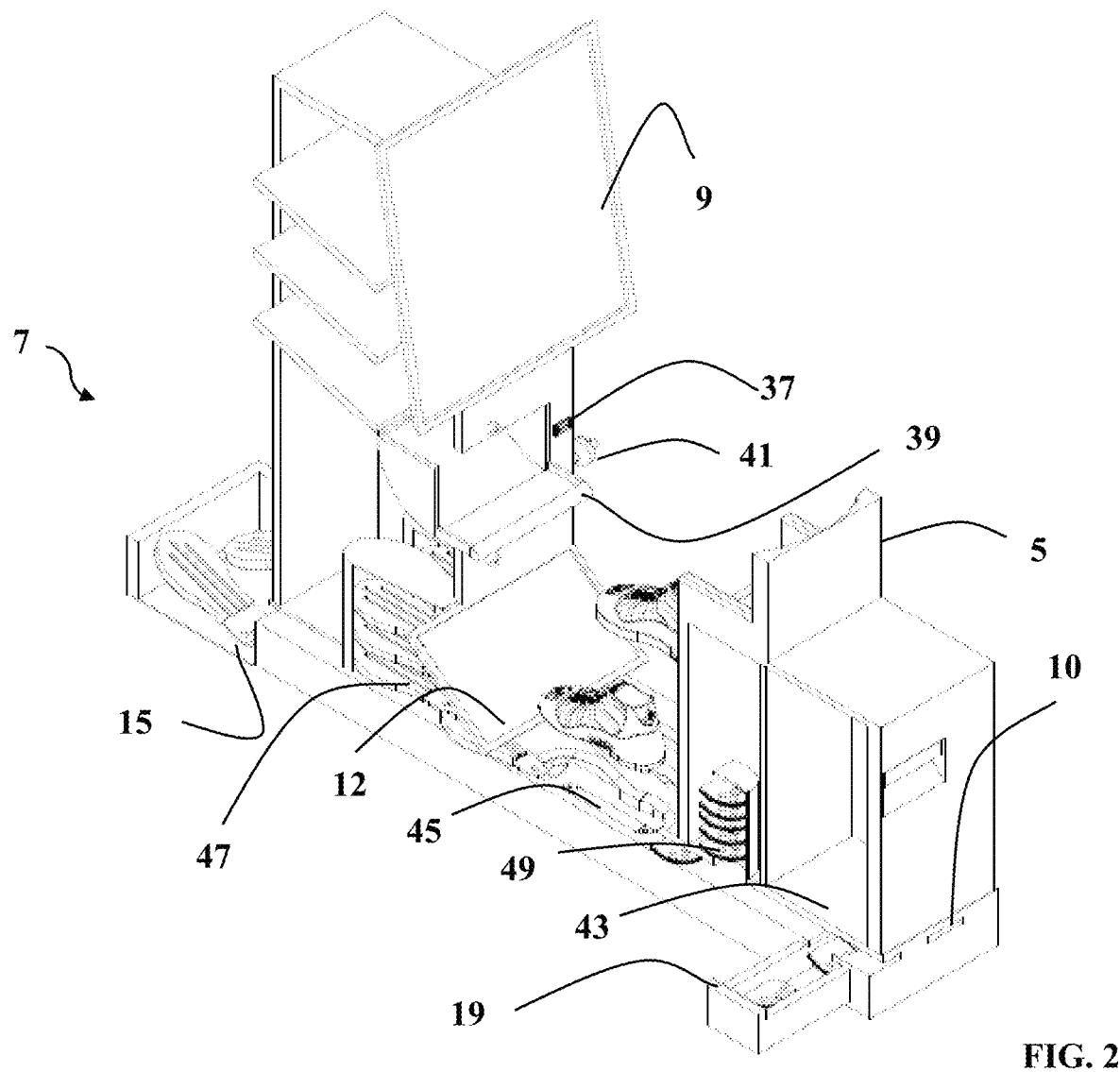
Figure 3:
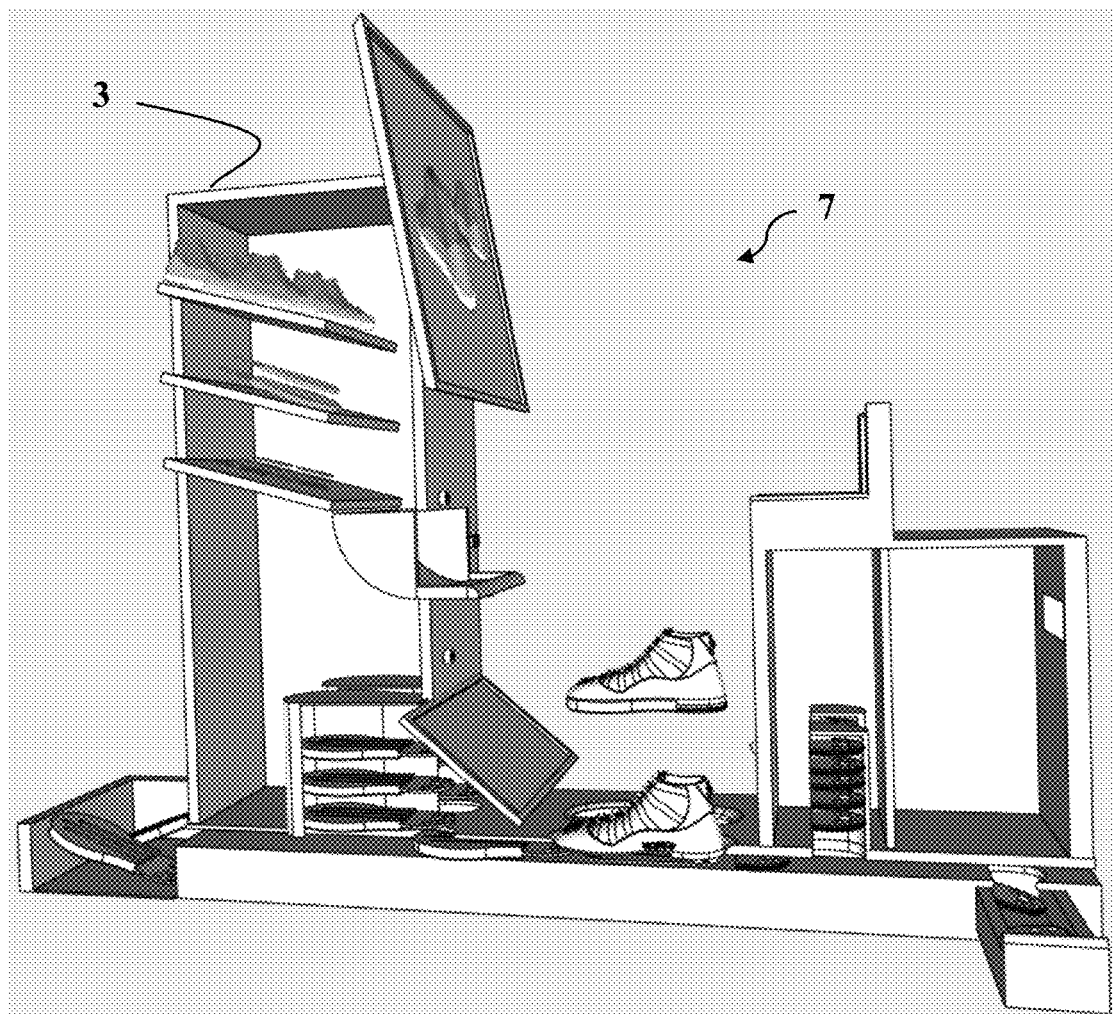
Figure 4:
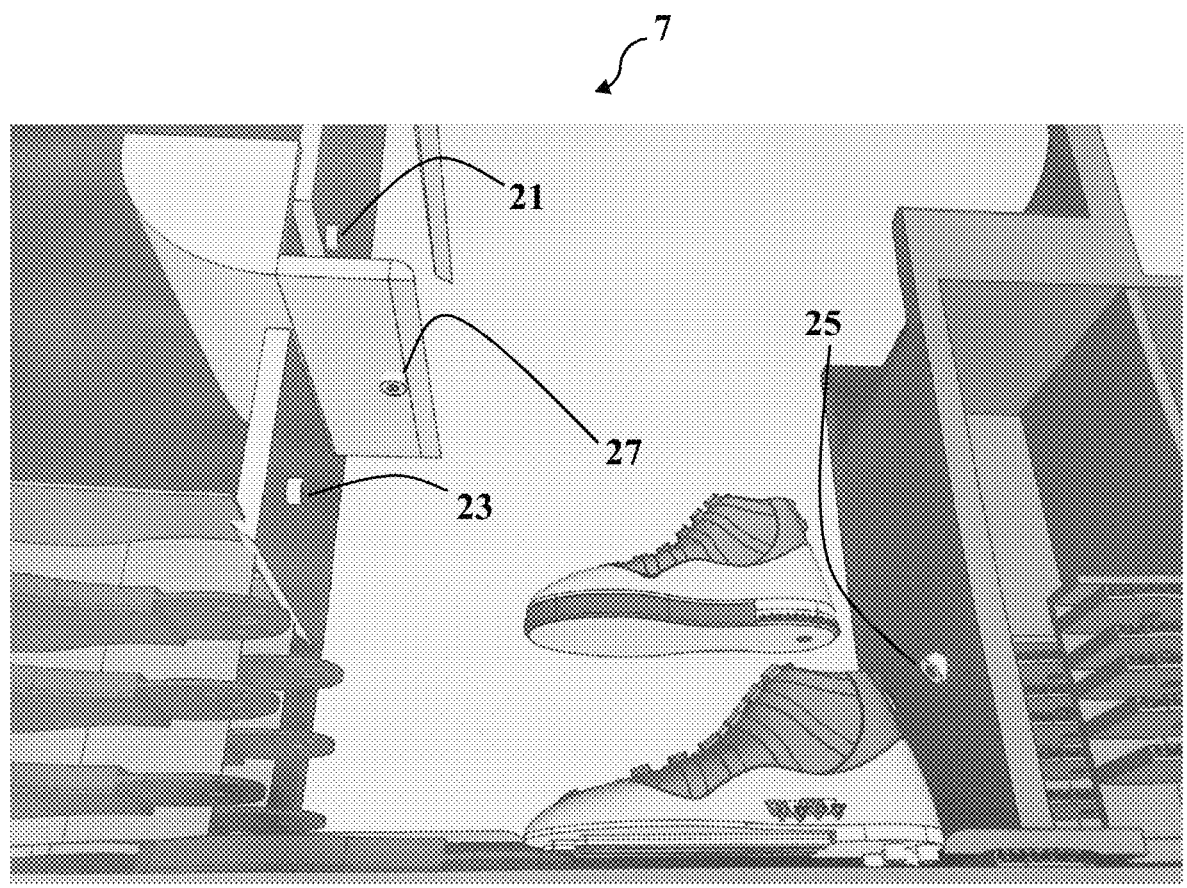
Figure 5:
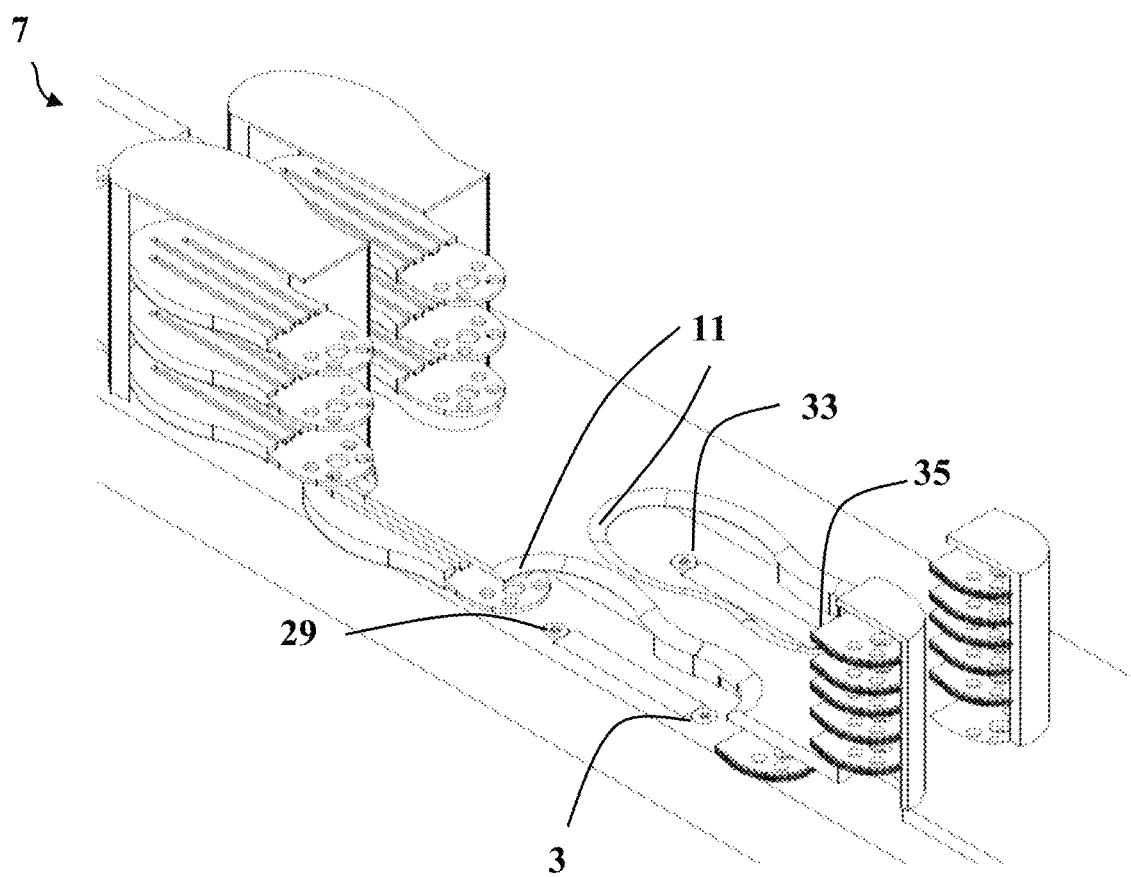

FIG. 1 is a front facing top view of the present invention.
FIG. 2 is a front facing side view of the present invention.
FIG. 3 is a left side view of the present invention.
FIG. 4 is a bottom view, zoomed in on the middle section, of the present invention.
FIG. 5 is a front facing side view, zoomed in on the receptacles detail, of the present invention.

DETAILED DESCRIPTION OF THE INVENTION

A. Overview

Turning now descriptively to the drawings, in which similar reference characters denote similar elements throughout the several views, FIGS. 1 through 5 illustrate a Chameleon Sole Station footwear apparatus 7, which comprises two receptacles 11, having a mechanism that removes and replaces interchangeable footwear sole parts as well as storage compartments 15, 19 for recycling old sole parts wherein said apparatus is comprised of a configuration to automatically replace the sole or partial sole of a pair or pairs of footwear.

B. Display Screen and Camera Scanners

In some versions, there is a display screen 9 and one or more multifunctional camera scanners 21, 23, 25, 27, 29, 31, 33, 35. In some versions, the display screen 9 displays one or more user interfaces (UIs) that enable a consumer to interact with the Chameleon Sole Station footwear apparatus 7. In some examples, the display screen 9 is provided as a touchscreen that displays one or more UIs and that is responsive to user input.

In this manner, the consumer can provide touch input to the Chameleon Sole Station footwear apparatus 7 through the display screen 9 to, among other things, make a selection, input information, and review footwear and footwear sole options. Although multiple multifunctional camera scanners 21, 23, 25, 27, 29, 31, 33, 35 are depicted in the example of FIGS. 1-5, implementations of the Chameleon Sole Station footwear apparatus 7 can be realized with a single camera or with no camera at all. In some examples, a camera 21, 23, 25, 27, 29, 31, 33, 35 can include, without limitation, a still camera, a video camera, an infra-red (IR) camera, or any appropriate camera with single or combined functionality.

C. Receptacles

Once the consumer has made a selection on the display screen 9 or utilized the foot scanning device 12, they can step into or place their shoes into the receptacles 10. Upon selection of the appropriate replacement footwear UI option, the consumer's Chameleon Sole footwear sole or sole part will be automatically replaced with new footwear soles or sole parts.

D. New Sole Dispensers

Once the consumer has selected footwear sole replacement, on some versions their sole or sole part will be removed and replaced with new parts supplied by the complete new sole dispenser 47 or the new sole heel dispenser 49. These dispensers form part of the sole removement and replacement mechanism.

E. Recycling Storage Compartments

Some versions of the Chameleon Sole Station footwear apparatus 7 will include a complete old sole storage recycling compartment 15 and an old sole heel recycling compartment 19. These compartments allow for the post-removal temporary storage of old footwear parts that consumers leave behind when obtaining new sole or partial soles for their Chameleon Sole footwear. These compartments will be regularly emptied, and their contents recycled. Consumers will also have the option of ejecting their used soles out of the sole ejection mechanism 10 of the Chameleon Sole Station footwear apparatus 7 should they desire to retain them.

F. Refurbish Request Storage Compartment

There is a refurbish request storage compartment 43 in some versions where consumers can deposit old footwear that they want to have refurbished, or retrofitted, with Chameleon Sole interchangeable soles. Using the display screen 9 UI interface, consumers will enter personal identification information (such as an email address) that will allow them to register their old footwear for refurbishment and enable unlocking of the refurbish request storage compartment 43 so that the old footwear can be temporarily stored before being picked up for offsite refurbishment.

G. Payment Reader

In some versions, the payment reader 37 reads payment information to enable submission of payment for the footwear, footwear sole or footwear sole part that is to be served by the Chameleon Sole Station footwear apparatus 7. In some examples, the payment reader is a traditional card reader that ingests a payment card (e.g., credit card, debit card, gift card) having payment information recorded thereon. Although a payment reader 37 is provided in some versions, it is contemplated that the Chameleon Sole Station footwear apparatus 7 can use any appropriate payment technique.

H. Foot Scanning Device

The foot scanning device 12 in some versions detects footwear size, footwear type and other foot-related data once a consumer's sock enrobed feet are placed upon it. Some versions include a built-in chair 5 to enhance consumer comfort while interacting with the Chameleon Sole Station footwear apparatus 7. Interfacing with the display screen 9 UI, the foot scanning device output is displayed on the display screen 9 based on the consumer's input selection.

I. Vending

In some versions, the Chameleon Sole Station footwear apparatus 7 features new footwear vending as well as standalone sole vending ("the vending machine"). The vending machine 3 includes an interface display screen 9 and a vending dispenser 39. The vending machine 3 houses devices, systems, footwear and footwear sole parts that can be dispensed to consumers through the vending dispenser 39. The vending machine is contemplated to be connected to a power source via a power cord 41, though some versions may use batteries or an alternative power source.

J. Foot Fixation Members

If deemed necessary, in some versions fixation members 45 such as magnets can be included to help hold footwear in position if the consumer desires, as an optional assist mechanism.

I claim:

1. A footwear apparatus, comprising:
   receptacles configured to receive footwear having interchangeable sole footwear parts;
   one or more cameras configured to detect that a consumer is physically present at least partially based on a depth determined using one or more images generated by the one or more cameras, the one or more cameras disposed in proximity to the receptacles;
   a computer-implemented foot scanning device configured to scan feet of the consumer to detect footwear size, footwear type and other foot-related data based on consumer's sock-enrobed feet, the computer-implemented foot scanning device disposed in front of and angled relative to the receptacles;
   a display screen configured to allow the consumer make a selection, input information, and review footwear and footwear sole options, the display screen disposed in front of and elevated in height relative to the receptacles; and
   one or more processors configured to:
   receive the footwear size, footwear type, other foot-related data, and input selections presented by the consumer,
   process the consumer input selections, and
   serve the consumer in response to consumer input selections.

2. The footwear apparatus of claim 1, wherein each of the receptacles includes a fixation member configured to fix the footwear in position in the receptacles.

3. The footwear apparatus of claim 2, wherein the fixation member is a magnet.

4. The footwear apparatus of claim 1, further including an old sole storage recycling compartment disposed in front of the receptacles, and an old sole heel storage recycling compartment and a refurbish request storage compartment disposed behind the receptacles.

5. The footwear apparatus of claim 1, further including a payment reader configured to process payment information from the consumer.

6. The footwear apparatus of claim 1, wherein the one or more processors are configured to determine that the consumer is physically present, and service the consumer being further in response to determining that the consumer is physically present.

7. The footwear apparatus of claim 1, further including a chair disposed behind and vertically spaced upward relative to the receptacles.

8. The footwear apparatus of claim 1, further including a vertical stack of new soles disposed in front of the receptacles.

9. The footwear apparatus of claim 8, further comprising a new sole dispenser configured to: receive a new sole from the vertical stack of new soles; and dispense the new sole received from the vertical stack of new soles.

10. The footwear apparatus of claim 1, further including a vertical stack of new sole heels disposed behind the receptacles.

11. The footwear apparatus of claim 10, further comprising a new sole heel dispenser configured to receive a sole heel from the vertical stack of new sole heels; and dispense the new sole heel received from the vertical stack of new sole heels.

12. A method for servicing a footwear having interchangeable sole footwear parts using the footwear apparatus of claim 1, the method comprising:
    receiving the footwear by the receptacles;
    taking images of the footwear using the one or more cameras;
    allowing the one or more processors to process the images of the footwear to determine that a consumer is physically present at least partially based on a depth determined using the images;
    scanning the feet of the consumer using the computer-implemented foot scanning device to generate consumer footwear data comprising one or more of the footwear size, the footwear type and the other foot-related data;
    displaying the consumer footwear data, and footwear and footwear sole options on the display screen;
    allowing the consumer to review the consumer footwear data and the footwear and footwear sole options on the display screen, and to input information and make a selection using the display screen;
    allowing the one or more processors to process the input information and the selection from the consumer; and
    servicing the footwear of the consumer in response to the input information and selection of the consumer.

13. A method for servicing a footwear having interchangeable sole footwear parts using a footwear apparatus, the method comprising:
    receiving the footwear in receptacles of the footwear apparatus;
    taking images of the footwear using one or more cameras of the footwear apparatus;
    processing the images of the footwear using one or more processors of the footwear apparatus to determine that a consumer is physically present at least partially based on a depth determined using the images of the footwear;

scanning feet of the consumer using a computer-implemented foot scanning device of the footwear apparatus to generate consumer footwear data comprising one or more of footwear size and footwear type;

displaying footwear sole options on a display screen of the footwear apparatus;

allowing the consumer to review the consumer footwear data and footwear sole options on the display screen, and to input information and make a selection using the display screen; and controlling the one or more processors configured to process the input information and the selection from the consumer to service the footwear in response to the input information and the selection of the consumer, wherein the one or more cameras are disposed in proximity to the receptacles;

wherein the computer-implemented foot scanning device is disposed in front of and angled relative to the receptacles and configured to scan the feet of the consumer;

wherein the display screen is disposed in front of and elevated in height relative to the receptacles; and wherein the one or more processors are configured to electrically communicate with the one or more cameras, the computer-implemented foot scanning device, and the display device.

14. The method of claim 13, wherein the interchangeable sole footwear parts comprise an interchangeable footwear sole and/or interchangeable footwear sole heel.

15. The method of claim 14, wherein the footwear apparatus further comprises a first housing disposed in front of the receptacles, the first housing comprising a vertical stack of new footwear soles.

16. The method of claim 15, wherein the footwear apparatus further comprises a new sole dispenser configured to: receive a new footwear sole from the first housing; dispense the new footwear sole received from the first housing; and/or have a sole replacing mechanism configured to remove the interchangeable footwear sole from the footwear, and/or install the new footwear sole received from the first housing to the footwear.

17. The method of claim 16, wherein the servicing footwear comprises dispensing the new footwear sole using the new sole dispenser, and/or removing the interchangeable footwear sole from the footwear and installing the new footwear sole received from the first housing to the footwear, using the new sole dispenser.

18. The method of claim 17, wherein the footwear apparatus further comprises an old footwear sole storage recycling compartment disposed in front of the receptacles and configured to receive and/or store the interchangeable footwear sole removed from the footwear.

19. The method of claim 18, wherein the footwear apparatus further comprises a sole ejection mechanism attached to the old sole storage recycling compartment and configured to eject the interchangeable footwear sole removed from the footwear.

20. The method of claim 19, further comprising storing the interchangeable footwear sole removed from the footwear in the old sole storage recycling compartment; or ejecting the interchangeable footwear sole removed from the footwear from the old sole storage recycling compartment using the sole ejection mechanism.

21. The method of claim 14, wherein the footwear apparatus further comprises a second housing disposed behind the receptacles, the second housing comprising a vertical stack of new footwear sole heels.

22. The method of claim 21, wherein the footwear apparatus further comprises a new sole heel dispenser configured to: receive a footwear sole heel from the second housing; dispense the new footwear sole heel received from the second housing; and/or have a sole heel replacing mechanism configured to remove the interchangeable footwear sole heel from the footwear and/or install the new footwear sole heel to the footwear.

23. The method of claim 22, wherein the servicing footwear comprises dispensing the new footwear sole heel received from the second housing, and/or removing the interchangeable footwear sole heel from the footwear and/or installing the new sole heel to the footwear, using the new sole heel dispenser.

24. The method of claim 23, wherein the footwear apparatus further comprises an old sole heel storage recycling compartment disposed behind the receptacles and configured to receive and store the interchangeable sole heel removed from the footwear.

25. The method of claim 24, wherein the footwear apparatus further comprises a sole heel ejection mechanism attached to the old sole heel storage recycling compartment and configured to eject the interchangeable footwear sole heel removed from the footwear from the old sole heel storage recycling compartment.

26. The method of claim 25, further comprising storing the interchangeable footwear sole heel removed from the footwear in the old sole heel storage recycling compartment; or ejecting the interchangeable footwear sole heel removed from the footwear from the old sole storage recycling compartment using the sole ejection mechanism.

27. The method of claim 13, wherein each of the receptacles comprises a fixation number, and wherein the method further comprises fixing the footwear in position in the receptacles using the fixation number.

28. The method of claim 13, wherein the footwear apparatus further comprises a payment reader configured to process payment information from the consumer, and wherein the method further comprises allowing the consumer to make a payment using the payment reader.

* * * * *